US005611769A

United States Patent [19]

Monroe

[11] Patent Number: 5,611,769
[45] Date of Patent: Mar. 18, 1997

[54] DETACHABLE CONNECTOR ASSEMBLY FOR USE WITH VIDEO CAMERA EQUIPPED MEDICAL INSTRUMENTS

[75] Inventor: Richard A. Monroe, Liverpool, N.Y.

[73] Assignee: Welch Allyn, Inc., Skaneateles Falls, N.Y.

[21] Appl. No.: 532,978

[22] Filed: Sep. 22, 1995

[51] Int. Cl.⁶ ..................................................... A61B 1/04
[52] U.S. Cl. ........................... 600/112; 600/132; 348/76; 348/73; 439/551
[58] Field of Search ........................ 348/76, 73; 600/112, 600/132, 110, 109; 439/551, 565

[56] References Cited

U.S. PATENT DOCUMENTS

| 3,462,727 | 8/1969 | Blight et al. |
| 3,663,926 | 5/1972 | Brandt. |
| 3,808,580 | 4/1974 | Johnson. |
| 4,834,667 | 5/1989 | Fowler et al. ........................... 439/321 |
| 4,853,773 | 8/1989 | Hibino et al. ........................... 358/98 |
| 4,856,495 | 8/1989 | Tohjoh et al. ........................... 128/6 |
| 4,863,396 | 9/1989 | Johnson ........................... 439/470 |
| 4,869,687 | 9/1989 | JOhnson ........................... 439/470 |
| 4,984,995 | 1/1991 | Tucker et al. ........................... 439/321 |
| 5,005,943 | 4/1991 | Fort ........................... 350/96.26 |
| 5,143,054 | 9/1992 | Adair ........................... 128/18 |

FOREIGN PATENT DOCUMENTS 63-304221 12/1988 Japan.

Primary Examiner—Gary F. Paumen
Attorney, Agent, or Firm—Harris Beach & Wilcox, LLP

[57] ABSTRACT

A video camera head for use with medical diagnostic instrumemts. A connector assembly, positioned at the outlet of the housing of the camera head, allows a video cable including a multi-conductor tightenable connector to be attached to and detached from the fragile internal wiring of the camera head without applying destructively high forces thereto. A mounting assembly, positioned at the inlet of the housing of the camera head, enclose and protects a video imaging chip while securely mounting the same in a predetermined position and orientation within the housing of the camera head.

16 Claims, 3 Drawing Sheets

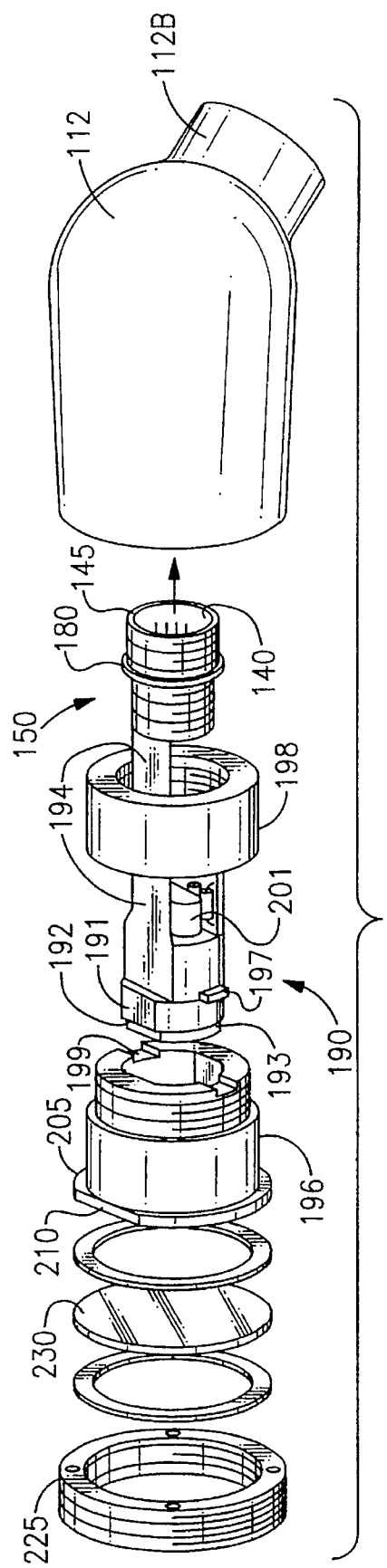
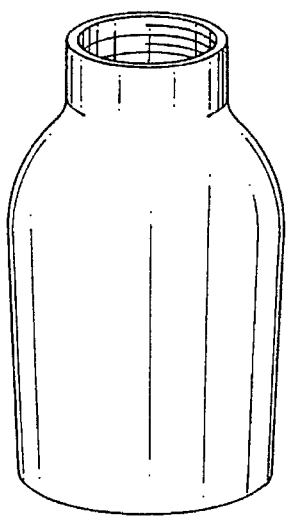
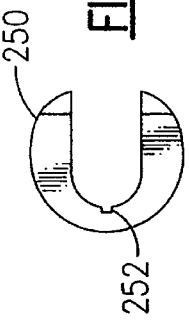
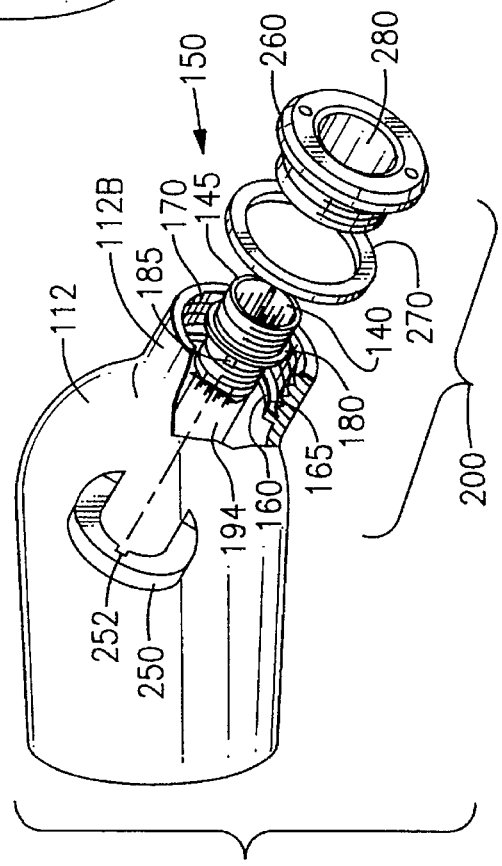

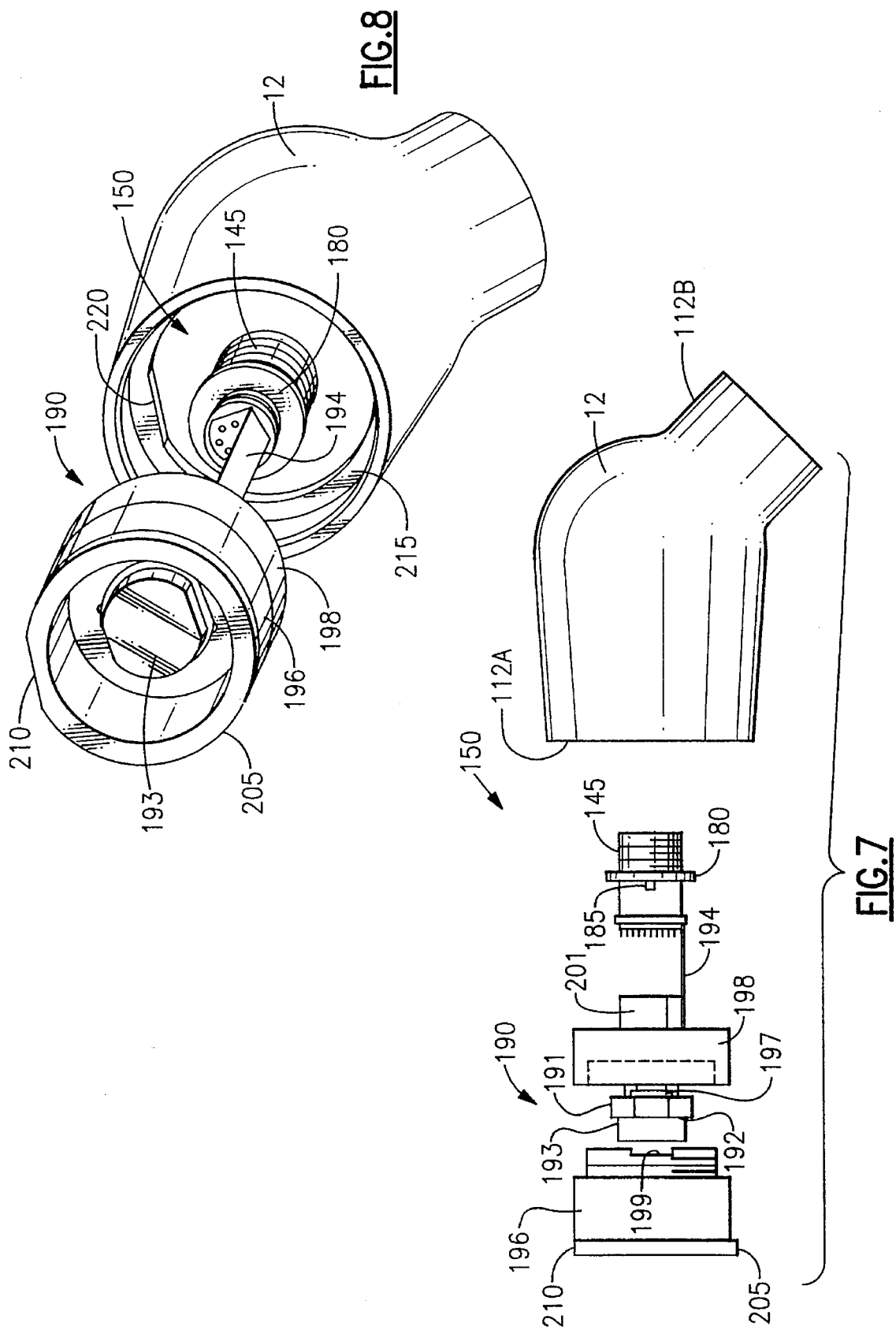

DETACHABLE CONNECTOR ASSEMBLY FOR USE WITH VIDEO CAMERA EQUIPPED MEDICAL INSTRUMENTS

BACKGROUND OF THE INVENTION

The present invention relates to video camera equipped medical diagnostic instruments, and is directed more particularly to a video connector assembly which facilitates the connection, disconnection and interchange of video camera devices to, from, and between such instruments.

As video imaging devices, particularly video imaging devices of the charge coupled or CCD type, have become smaller, more reliable and less expensive, it has become feasible to equip a wide variety of medical diagnostc instruments for use with video cameras. Among the many instruments which have been equipped in this way are otoscopes, ophthalmoscopes, episcopes, and sigmoidoscopes, among others. Examples of instruments of this type are described in U.S. Pat. No. 4,853,773 (Hibino et al.);U.S. Pat. No. 4,856,495 (Tohjoh); and U.S. Pat. No. 5,143,054 (Adair).

In many instruments of the above-described type which were known or used prior to the present invention, it was common practice to design an instrument to operate with a single imaging system and to build that imaging system into the instrument as an integral, dedicated part thereof. In many instruments of the latter type, such as those described in the above cited Tohjoh et al. patent and in U.S. Pat. No. 5,005,943 (Fort), little concern was shown for using the video imaging system with other instruments or even for providing the imaging system with a detachable connector plug.

In other instruments of the above-described type which were known or used prior to the invention, the video imaging system was provided with a detachable connector plug, but not for the purpose of making the imaging system usable with different instruments. An example of an instrument of the latter type is shown in Japanese Kokai 63-304221, published Dec. 12, 1988 (Okabe).

None of the instruments or instrument systems known prior to the present invention, however, has included a video camera head which may be used as a compact, cordless module which may be easily connected, disconnected and interchanged. More particularly, no prior art instrument has included a video camera head having an imaging or input end which may be easily attached to and detached from any of a variety of different instruments, and having an output end with a connector assembly which may be easily attached to and detached from the video cable that conducts electrical signals to and from the video head. As a result, video camera heads used prior to the invention have been encumbered by video cables which make them inconvenient to handle, interchange, disassemble for servicing, or pack and unpack for transport.

BACKGROUND OF THE INVENTION

In accordance with the present invention there is provided an improved video camera head which has none of the above-mentioned undesirable features. More particularly, there is provided an improved modular video camera head having an input end which may be easily attached to and detached from any of a variety of different instruments, and having an output end which includes a connector assembly that allows the video head to be easily attached to and detached from a video cable to facilitate the interchange, packing and unpacking and servicing thereof.

Generally speaking, the present invention contemplates a video camera head having an input end which is adapted to thread onto a standard "C mount" adapter which is, in turn, adapted to clampingly engage instruments of a variety of different types. Because such adapters are designed to be used with a variety of different optical or lens assemblies, they allow the video head to couple, without change, to any of a variety of different medical diagnostic instruments such as otoscopes, episcopes, etc.

The present invention also contemplates a video camera head having an output end which includes an improved connector assembly to which a multi-conductor video cable may be easily attached to and detached, without generating destructively high forces between itself and the internal wiring of the video head. This, in turn, allows the video head to be easily and safely broken down into a compact, cordless module that may be easily packed and unpacked, and that may be easily attached to and detached from the instrument with which it is used before the video cable is reattached.

In accordance with the invention, the connector assembly is constructed so that it may be easily and fully detached from the housing of the video head. This detachability, in turn, allows the internal video circuitry of the video head to be removed for servicing or modification as required and then easily and quickly re-inserted and reattached. This capability provides an important advantage over prior video connector structures, which are designed either not to permit the video cable to be disconnected at all or to not permit the internal circuitry of the video head to be removed without special tools.

In the preferred embodiment, the video camera head of the invention includes a housing having an outlet opening that defines an internal retaining shoulder. This opening is dimensioned so that a video connector plug having a circumferential flange can pass therethrough from the inside. Once the latter has passed through the outlet opening its circumferential flange is locked in place with respect to the retaining shoulder by a U-shaped spacer and a retaining collar. Advantageously, the spacer has a shape such that it may be inserted from a direction roughly perpendicular to the longitudinal axis of the connector plug, while the latter is hanging loosely within the opening. The spacer also includes a key slot for engaging a matching key structure on the connector plug, thereby preventing the latter from rotating with respect to the spacer. Once tightened in place by the retaining collar, the entire assembly is prevented from rotating with respect to the video head and the internal wiring thereof. This, in turn, allows an external connector plug to be connected to and disconnected from the connector assembly as required without damaging the internal wiring of the video head.

The preferred embodiment of the video camera head of the invention also includes a mounting structure which is adapted to enclose, mount and protect the video camera or imaging chip and the fragile elements that are located immediately adjacent thereto. This protective mounting structure, and the video housing within which it fits, are provided with mating orienting and positioning structures which assure that the mounting structure comes to rest within the housing in a predetermined position and with a predetermined orientation. This not only assures a solid protective contact between the mounting and housing, it also facilitates the use of embodiments of the invention which include a housing having an anti-rotation key structure.

DESCRIPTION OF THE DRAWINGS

Other objects and advantages of the invention will be apparent from the following description and drawings, in which:

FIG. 3 is an oblique exploded view of the contents of the video camera head of FIG. 2;

FIG. 4 is an oblique view of an alternative housing suitable for use with the video camera head of FIG. 3;

FIG. 5 is a partly assembled, partly cutaway view of the video head of FIG. 3;

FIG. 6 is a plan view of the U-washer shown in FIG. 5;

FIG. 7 is an exploded side view of the video chip mounting structure shown in FIG. 3; and FIG. 8 is an exploded oblique view showing how the mounting structure of FIG. 7 fits into the housing of the video head of the invention.

DESCRIPTION OF THE PREFERRED EMBODIMENTS

Figure 1:
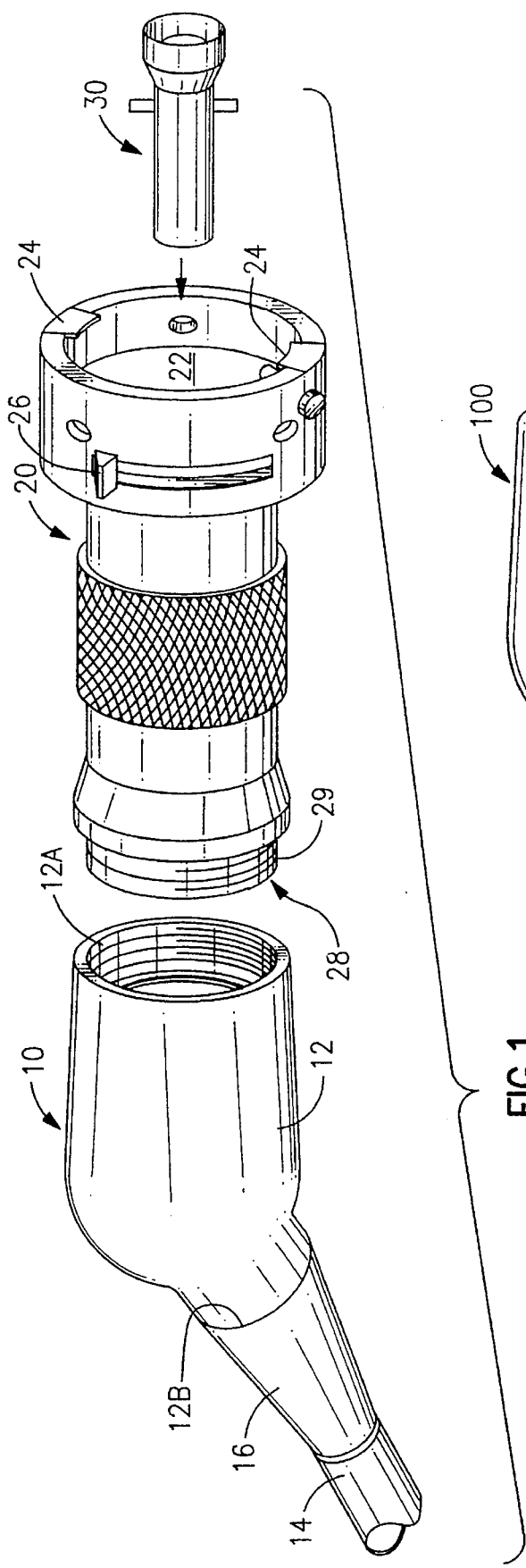
FIG. 1 is an exploded view of a "C-Mount" adapter, together with a prior art video camera head suitable for use therewith.

Referring to FIG. 1 there is shown a video camera head 10 of a type known in the art. This camera head includes housing 12 having an imaging or input end 12A for connection to a medical diagnostic instrument, such as an otoscope or episcope (not shown). Images formed by the instrument are typically directed into input 12A through a conventional "C-Mount" adapter 20. The latter adapter is constructed to accept any one of a plurality of autoclavable optical inserts or lens assemblies, such as that shown at 30 in FIG. 1, each of which is arranged to provide a focused image to video camera head 10 when used with a particular instrument.

"C-mount" adapter 20 has an input opening 22 that includes a pair of clamping elements 24 which are opened and closed by an actuating lever 26 to clamp onto or release a mating portion of the instrument. Adapter 20 also has an output end 28 that includes a threaded surface 29 which is adapted to thread into opening 12A of video head 10. When adapter 20 is secured to both video head 10 and an instrument, the three elements together comprise a video equipped instrument of a type dependent upon the type of instrument that is clamped in place within adapter input opening 22.

Included within video camera head 10 of FIG. 1 is a video image sensor, such a CCD array, together with certain timing and control circuits therefor, neither of which is shown in FIG. 1. The conductors which supply power and control signals to this video circuitry, and the conductors which supply the video signals produced by this circuitry to external video processing circuitry (not shown), are typically formed into a ribbon or other multi-conductor cable located within housing 12. In prior art video camera heads, such as that shown in FIG. 1, the conductors of this internal cable were brought out to or through output end 12B thereof, where they were coupled to or merged into a multi-conductor video cable 14. In both cases, a stress relief member 16 such as an elastomeric boot was permanently secured between housing 12 and cable 14 to prevent externally general stresses from being transmitted from cable 14 to the internal wiring of video head 10.

Figure 2:
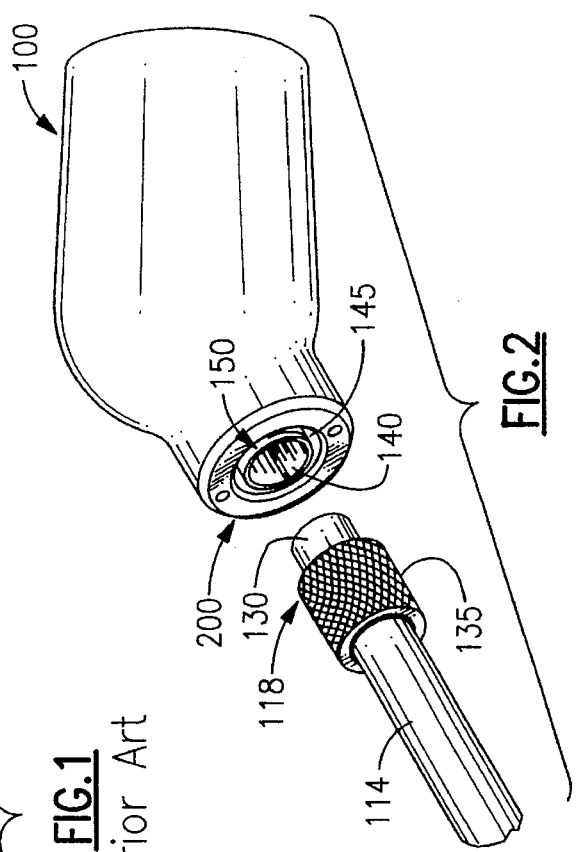
FIG. 2 is an oblique exploded assembly view of a video camera head constructed in accordance with the invention, together with a conventional video/cable suitable for use therewith.

Referring to FIG. 2 there is shown an external assembly view of a video camera head 100 which has been constructed in accordance with the present invention. Except as will be explained more fully presently, video head 100 is generally similar to video head 10 of FIG. 1 and is used, in generally the same way, in conjunction with a C-mount adapter such as adapter 20 and optics 30 of FIG. 1. Video head 100 of FIG. 2 differs from video head 10 of FIG. 1, however, in that it includes an output connector assembly 200 which is adapted to be detachably coupled to the conventional end connector 118 of a conventional multi-conductor video cable 114 of a type well known in the art. End connector 118 is preferably of the type which includes a multi-pin connector plug 130 which is pushed into the mating connector plug 140 of video output connector 150 of assembly 200. Once firmly seated, a knurled knob 135 with interior threads is then threadedly tightened or otherwise locked into engagement with the exterior threads of shell 145 of connector plug 140. This tight locked connection assures an electrical contact to and through plug 140 which is far superior to that provided by simple plug-in connectors.

When end connector 118 is threadedly secured to video output connector 150 of assembly 200, the electrical contacts between the conductors of cable 114 and the corresponding conductors of video head 100 are as good as those established by the non-detachable cable shown in FIG. 1. When end connector 118 is detached, however, as shown in FIG. 2, video head 100 is released for use as a compact module that may be easily added to and removed from a medical diagnostic instrument assembly without the encumbrance of an attached video cable. Without the encumbrance of a video cable, video head 100 may also be easily packed and unpacked for transport or even disassembled for servicing or modification. And, when it is ready to be reconnected to a video cable, video head may be attached to a different video cable than was originally attached thereto, as for example; a cable that is longer or shorter than the original cable.

To the end that the above-mentioned advantages may be provided without creating the risk that repeated detachments and reattachments of a video cable will damage the internal wiring of video head 100, the present invention provides an improved connector assembly 200 which is best understood with reference to FIGS. 3, 5 and 6. Referring first to FIG. 5, connector assembly 200 will be seen to include a housing 112 having an output end 112B which defines an outlet opening 160 and a retaining shoulder 165. Opening 160 and shoulder 165 are located at the inner end of a larger, threaded opening 170 which is adapted to receive a threaded collar 260 to be more fully described later.

Connector assembly 200 of the invention also includes a video output connector 150, such as a DIN connector, having a multi-pin plug portion 140 and a threaded shell portion 145 from which extends a circumferentially disposed flange 180 and a radially disposed key 185. Opening 160 is preferably large enough that output connector 150 (including flange 180) may be passed therethrough and hang loosely within threaded opening 170. This ability to pass through opening 160 is important because (as shown in FIG. 3), it allows the video assembly 190 of video head 100, including image sensor 192 and a video ribbon connector 194, with output connector 150 attached, to be easily inserted into video housing 112 as a complete unit. (As will be explained more fully later, the distal portion of assembly 192 is preferably enclosed in a novel mounting structure including mounting members 196 and 198 which seat against a specially provided shoulder 215 formed in the interior of housing 12.) Conversely, so long as output connector 150 is not secured in place within opening 170, video assembly 190 may be easily removed from video head 100. Thus, as previously explained, the connector assembly of the invention allows the video head with which it is used to be easily assembled and disassembled for servicing or modification.

To the end that end connector 150 may be so securely attached to housing 112 that cable 114 may be safely attached to and detached from video camera head 100, without disturbing the connections between ribbon cable 194 and plug 140, connector assembly 200 is provided with a generally U-shaped spacer 250, a retaining collar 260 and (optionally) a compressible washer 270. As connector assembly 200 is installed, spacer 250 is pushed into opening 170 and over shell 145 from a direction roughly perpendicular to the longitudinal axis thereof. This direction is selected so a key slot 252 cut in the rear of spacer 250 engages key 185 of shell 145 just behind circumferential flange 180 thereof. The entry of spacer 250 into opening 170, with shell 145 in place, is facilitated by the non-circular shape thereof, as is best shown in FIG. 6. This non-circular shape, which is characterized by a smaller radial dimension in those parts of spacer 250 which are relatively closed to key slot 252 than in those parts of spacer 250 which are relatively distant from key slot 252, allows spacer 250 to be inserted at the angle necessary to fit under flange 180 in spite of the latter being located below the outer edge of opening 170.

Once space 250 has been snapped into place and come to rest on retaining shoulder 165, connector 150 is secured in place by inserting compressible washer 270 thereover and then threading retaining collar 260 snugly in place within opening 170. As this occurs the frictional force acting between connector 150, spacer 250, flange 180 and washer 270 becomes so great that connector 150 is effectively locked in a fixed position with respect to housing 112. This, in turn, assures that the torque which is later applied thereto by the attachment and detachment of end connector 118 of cable 114 is not transmitted to and does not disturb the fragile connections between ribbon cable 194 and connector 140. In so doing, assembly 200 assures the achievement of one of the most important objectives of the invention. Washer 270 serves the additional function of sealing the interior of video head 10 against the entry of contaminants.

In the event that the materials used in connector assembly 200 do not generate frictional forces large enough to produce the above described result, this result may be assured by including in retaining shoulder 165 or elsewhere an anti-rotation structure that is able to engage the open portion of spacer 250. Such a structure might, for example, include a key type projection on or from retaining shoulder 165. It will be understood that this and similar anti-rotation means are within the contemplation of the present invention.

One particularly desirable secondary feature of the present invention is that, when it is fully assembled, as shown in FIG. 2, the outermost end of output connector 150 lies in or below the outermost surface of retaining collar 260. This recessed position serves to protect both the threaded surface of shell 145 and the pins of plug 140 from accidental damage resulting from unintended impacts during use, packing, etc. As explained previously, this recessed position is related to and made possible by the non-circular shape of spacer 250.

Referring to FIGS. 3, 7 and 8, there will now be described video mounting assembly 190 of the video head of the present invention. As is best shown in FIGS. 3 and 7, assembly 190 includes a two part mounting structure including mounting members 196 and 198. Positioned between these mounting members is a ceramic substrate 191 upon which is mounted a video imaging chip 192 (seen edge on) which is, in turn, covered by a transparent glass cover plate 193. Signals are coupled between chip 192 and plug 140 via multi-conductor ribbon cable 194.

To the end that imaging assembly 191–193 may be securely mounted between mounting members 196 and 198, substrate 191 is provided with projecting tabs 197 which are sized and positioned to fit into a matching pair of slots 199 in mounting member 196. When the imaging assembly is positioned between members 196 and 198, the latter are threaded together to form a closed protective housing, best shown in FIG. 8, through which cable 194 and connector 150 project.

In accordance with a feature of the present invention, mounting member 196 is provided with a outwardly projecting rim 205 having a key structure here comprising a flattened surface region 210. Cooperating with rim 205 and key 210 are mating structures 215 and 220 formed within housing 12. Together these mating structures assure that video assembly 190 fits into the video head 10 in only a single position and with only a single orientation. Once in this position and orientation assembly 190 is preferably locked in place by a threaded retaining ring 225, best shown in FIG. 3, together with any intervening structures such as planar window 280 and any associated sealing gaskets. It will therefor be seen that, once the video head of the invention is fully assembled, fragile imaging chip 192 and associated components are immobilized within and surrounded by both members 196–198 and by housing 12.

While the present invention has been described with reference to one or more specific embodiments, it will be understood that the true spirit and scope of the present invention should be determined with reference to the appended claims.

What is claimed is:

1. A connector assembly for a video camera head having a threaded outlet opening that includes an internal retaining shoulder, a video output connector having a circumferential flange, a key structure and a plurality of output pins connected to a video imaging device, including, in combination:

a U-shaped spacer shaped to engage said key structure and flange and to seat on said retaining shoulder;

a retaining collar adapted to thread into said outlet opening and secure said spacer and said connector in place with respect to the imaging head;

whereby an external cable may be attached to and detached from said video output connector without subjecting the connections between said pins and said imaging device to forces high enough to damage said connections.

2. The connector assembly of claim 1 in which said retaining shoulder defines an opening large enough to permit said flange to pass therethrough, but not large enough to permit said spacer to pass therethrough.

3. The connector assembly of claim 1 in which said spacer defines a key receiving structure, and in which said spacer has a smaller radial dimension in those parts of the spacer that are relatively close to said key receiving structure than in those parts of the spacer that are relatively distant from said key receiving structure.

4. The connector assembly of claim 1 further including a compressible member disposed between said retaining collar and said flange.

5. The connector assembly of claim 1 in which said connector and said collar are so sized and shaped that, when said collar is secured to said imaging head, the outer surface of said collar and the outer surface of said connector are approximately flush with one another.

6. The connector assembly of claim 1 in which said key structure and said spacer are positioned between said flange and said retaining shoulder.

7. A video camera head including a housing, a video imaging device supported within said housing, a video connector having a plurality of output pins and a multi-conductor cable for connecting said imaging device to said output pins; said video connector being of the type including a connector shell having a circumferentially disposed flange and a radially disposed key structure; said housing including a threaded opening through which said connector shell may project, and a retaining shoulder, characterized by:

a generally U-shaped spacer adapted to fit over said shell and to engage said key structure and said flange;

a threaded retaining collar adapted to threadedly engage said threaded opening while pressing said flange and spacer against said shoulder;

whereby a video cable connector may be threadedly secured to said connector shell without damaging the connections between said multi-conductor cable and said output pins.

8. The video camera head of claim 7 in which said U-shaped spacer is so shaped that it may be slipped over said connector and into engagement with said key structure while said connector shell hangs loosely within said threaded opening.

9. The video camera head of claim 7 in which said spacer defines a key structure receiving slot, and in which said spacer has a radial dimension that is smaller in those parts of the spacer that are relatively close to said slot than in those parts of the spacer which are relatively distant from said slot.

10. The video camera head of claim 1 further including a compressible gasket disposed between said retaining collar and said flange.

11. The video camera head of claim 7 in which said housing, said connector and said collar are so shaped that, when the imaging head is fully assembled, the outer surface of said collar and the outer surface of said connector lie approximately in the same plane.

12. The video camera head of claim 7 in which said key structure and said spacer are both located along the same surface of said flange.

13. A video camera head having a housing defining an inlet opening including, in combination:

a video imaging chip for receiving an optical image and converting said image to an electrical signal;

first and second mounting members for mounting and enclosing said imaging chip;

positioning means, formed in at least one of said mounting members and said housing, for positioning said imaging chip in a predetermined position within said housing.

14. The camera head set forth in claim 13 further including orienting means, formed in at least one of said mounting members and said housing, for establishing a predetermined orientation between said chip and said housing.

15. A video camera head defining an inlet opening and an outlet opening including, in combination:

a video imaging chip for receiving an optical image and converting said image to a video signal;

a multi-conductor tightenable connector plug, said plug having a circumferential flange and a key structure;

a multi-conductor cable for transmitting electrical signals including said video signal between said chip and said connector plug;

first and second mounting members for mounting and enclosing said imaging chip;

positioning means, formed in at least one of said mounting members and said inlet opening, for positioning said imaging chip in a predetermined position within said housing;

a retaining shoulder formed in said outlet opening;

a U-shaped spacer shaped to engage said key structure and to seat on said retaining shoulder; and a retaining collar adapted to thread into said outlet opening and secure said spacer and said connector plug in place with respect to said housing.

16. The video camera head of claim 15 in which said mounting members are adapted to thread into one another with said imaging chip positioned therebetween.

* * * * *